(12) United States Patent
Shiao et al.

(10) Patent No.: US 9,540,822 B2
(45) Date of Patent: Jan. 10, 2017

(54) COMPOSITE NANOPARTICLES FOR ROOFING GRANULES, ROOFING SHINGLES CONTAINING SUCH GRANULES, AND PROCESS FOR PRODUCING SAME

(75) Inventors: Ming Liang Shiao, Collegeville, PA (US); Gregory F. Jacobs, Oreland, PA (US); Sean X. Zhou, Collegeville, PA (US)

(73) Assignee: CertainTeed Corporation, Malvern, PA (US)

( * ) Notice: Subject to any disclaimer, the term of this patent is extended or adjusted under 35 U.S.C. 154(b) by 1248 days.

(21) Appl. No.: 12/950,460

(22) Filed: Nov. 19, 2010

(65) Prior Publication Data

US 2011/0159240 A1 Jun. 30, 2011

Related U.S. Application Data

(60) Provisional application No. 61/264,034, filed on Nov. 24, 2009.

(51) Int. Cl.
| | |
|---|---|
| *E04D 7/00* | (2006.01) |
| *B01J 2/00* | (2006.01) |
| *B82Y 30/00* | (2011.01) |
| *E04D 1/00* | (2006.01) |

(52) U.S. Cl.
CPC ............... *E04D 7/005* (2013.01); *B01J 2/006* (2013.01); *B82Y 30/00* (2013.01); *E04D 2001/005* (2013.01); *Y10T 428/2438* (2015.01); *Y10T 428/2991* (2015.01)

(58) Field of Classification Search
CPC .................................................... E04D 7/005

USPC ........................................................ 427/212
See application file for complete search history.

(56) References Cited

U.S. PATENT DOCUMENTS

| | | |
|---|---|---|
| 1,677,701 A | 7/1928 | Alton |
| RE19,372 E | 11/1934 | Walton |
| 2,001,448 A | 5/1935 | Beasley |
| RE20,295 E | 3/1937 | Fisher |
| 2,142,540 A | 1/1939 | Veazey |
| 2,379,358 A | 6/1945 | Jewett |
| 2,591,149 A | 4/1952 | Grove |
| 2,614,051 A | 10/1952 | Buzzell et al. |
| 2,695,851 A | 11/1954 | Lodge |
| 2,799,241 A | 7/1957 | Wurster |
| 2,898,232 A | 8/1959 | Miller et al. |
| 2,927,045 A | 3/1960 | Lodge et al. |
| 2,981,636 A | 4/1961 | Lodge et al. |

(Continued)

FOREIGN PATENT DOCUMENTS

| | | |
|---|---|---|
| EP | 0003302 | 8/1997 |
| EP | 1889810 A1 | 2/2008 |

(Continued)

OTHER PUBLICATIONS

Tyler Wireman, "The Aging Process of Shingles," 4 pgs., date unknown.

(Continued)

*Primary Examiner* — Tabatha Penny
(74) *Attorney, Agent, or Firm* — Paul & Paul (57) ABSTRACT

Roofing granules are prepared by coating granule cores with a coating material including composite nanoparticles and curing the coating layer to dissolve the aggregate binder and disperse the nanoparticles in the coating.

17 Claims, 2 Drawing Sheets

(56) References Cited

U.S. PATENT DOCUMENTS

| | | | |
|---|---|---|---|
| 2,986,476 A | 5/1961 | Larssen | |
| 3,089,824 A | 5/1963 | Wurster | |
| 3,117,027 A | 1/1964 | Lindolf et al. | |
| 3,196,827 A | 7/1965 | Wurster et al. | |
| 3,207,824 A | 9/1965 | Wurster et al. | |
| 3,241,520 A | 3/1966 | Wurster et al. | |
| 3,253,944 A | 5/1966 | Wurster | |
| 3,255,031 A | 6/1966 | Lodge et al. | |
| 3,397,073 A | 8/1968 | Fehner | |
| 3,479,201 A | 11/1969 | Sloan | |
| 3,507,676 A | 4/1970 | McMahon | |
| 3,528,842 A | 9/1970 | Skadulis | |
| 3,752,696 A | 8/1973 | Beyard | |
| 3,918,407 A | 11/1975 | Greenberg | |
| 3,961,628 A | 6/1976 | Arnold | |
| 3,985,540 A | 10/1976 | Fein et al. | |
| 4,092,441 A | 5/1978 | Meyer et al. | |
| 4,378,408 A | 3/1983 | Joedicke | |
| 4,623,588 A | 11/1986 | Nuwayser et al. | |
| 5,022,897 A | 6/1991 | Balcar et al. | |
| 5,147,686 A | 9/1992 | Ichimura et al. | |
| 5,180,585 A | 1/1993 | Jacobson et al. | |
| 5,225,123 A | 7/1993 | Torobin | |
| 5,356,664 A | 10/1994 | Narayan et al. | |
| 5,366,767 A | 11/1994 | Howard | |
| 5,411,803 A | 5/1995 | George et al. | |
| 5,427,793 A | 6/1995 | Bigham et al. | |
| 5,503,840 A | 4/1996 | Jacobson et al. | |
| 5,573,782 A | 11/1996 | Bigham et al. | |
| 5,595,750 A | 1/1997 | Jacobson et al. | |
| 5,595,813 A | 1/1997 | Ogawa et al. | |
| 5,599,586 A | 2/1997 | Israel | |
| 5,616,532 A | 4/1997 | Heller et al. | |
| 5,840,111 A | 11/1998 | Wiederhoft et al. | |
| 5,876,683 A | 3/1999 | Glumac et al. | |
| 5,888,930 A | 3/1999 | Smith et al. | |
| 6,037,289 A | 3/2000 | Chopin et al. | |
| 6,063,849 A | 5/2000 | Morris et al. | |
| 6,143,318 A | 11/2000 | Gilchrist et al. | |
| 6,156,245 A | 12/2000 | Takebayashi et al. | |
| 6,214,466 B1 | 4/2001 | Joedicke | |
| 6,245,381 B1 | 6/2001 | Israel | |
| 6,362,121 B1 | 3/2002 | Chopin et al. | |
| 6,413,581 B1 | 7/2002 | Greenberg et al. | |
| 6,465,088 B1 | 10/2002 | Talpaert et al. | |
| 6,548,145 B2 | 4/2003 | Joedicke | |
| 6,548,264 B1 | 4/2003 | Tan et al. | |
| 6,569,520 B1 | 5/2003 | Jacobs | |
| 6,607,781 B2 | 8/2003 | Joedicke | |
| 6,610,135 B1 | 8/2003 | Ohmori et al. | |
| 6,653,356 B2 | 11/2003 | Sherman | |
| 6,797,277 B2 | 9/2004 | Heier et al. | |
| 6,872,402 B2 | 3/2005 | Mangold et al. | |
| 6,905,698 B1 | 6/2005 | Aldcroft et al. | |
| 7,217,407 B2 | 5/2007 | Zhang | |
| 2002/0098110 A1 | 7/2002 | Graham et al. | |
| 2002/0160151 A1 | 10/2002 | Pinault et al. | |
| 2003/0037698 A1 | 2/2003 | Kiik et al. | |
| 2003/0068469 A1 | 4/2003 | Aschenbeck et al. | |
| 2003/0108668 A1 | 6/2003 | Joedicke | |
| 2004/0255548 A1 | 12/2004 | Hong et al. | |
| 2004/0258835 A1 | 12/2004 | Hong et al. | |
| 2005/0053745 A1 | 3/2005 | Bartek et al. | |
| 2006/0251807 A1 | 11/2006 | Hong et al. | |
| 2007/0065641 A1* | 3/2007 | Joedicke | 428/143 |
| 2007/0148340 A1 | 6/2007 | Kalkanoglu et al. | |
| 2007/0148342 A1 | 6/2007 | Kalkanoglu et al. | |
| 2008/0026183 A1* | 1/2008 | Vanpoulle et al. | 428/143 |
| 2008/0118640 A1 | 5/2008 | Kalkanoglu et al. | |
| 2008/0241472 A1* | 10/2008 | Shiao et al. | 428/144 |
| 2009/0131517 A1 | 5/2009 | Height et al. | |
| 2011/0003157 A1 | 1/2011 | Besson et al. | |

FOREIGN PATENT DOCUMENTS

| | | |
|---|---|---|
| JP | 61176501 | 8/1986 |
| JP | 2004162482 | 6/2004 |
| WO | 0020346 A1 | 4/2000 |

OTHER PUBLICATIONS

Technical Bulletin Asphalt Roofing Manufacturers Association "Algae Discoloration of Roofs," Catalogue No. 217-PR89, 1 pg., (Calverton, MD), May 1997.

Copper Development Association Inc., "Copper Blocks Ugly Bugs," 2 pgs., Winter 1995.

Johns Manville Roofing Systems Group, "Roofing Granules" Sheet ID: 3004,6 pgs., (Denver, CO) Issued Jan. 11, 2001.

Minerals Research & Recovery, Inc., "Roofing Granules," 2 pgs., (Tucson, AZ), date unknown.

I. Colon, Phd.D.; E. L. Kuusisto, and HansenTroy Corporation, "Location Affects Performance of Biocide-Containing Paints," Florham Park, NJ.

Karen Winkowski, Ph.D., "Biocide Optimization Blend of Actives," International Speciality Products, Wayne, NJ.

Shawn Holiday, "Algae on the Roof: A Growing Problem," Posted on Aug. 23, 2004.

G. Beestman, "Microencapsulation of Solid Particles," H. B. Scher, Ed., Marcel Dekker, Inc., pp. 31-54, New York 1999.

Qingyuan Hu, "Synthesis and Characterization of Functionalized Mesoporous Silica by Aerosol-Assisted Self-Assembly," Chemical & Biomelecular Engineering, # 574 (2006).

Gifty Osei-Prempel, et al., "Synthesis and Application of Fluorocarbon Functionalized Mesoporous Silica" Materials Engineering and Sciences Division # 574 (2006).

Rhonda Stroud, "Silica Sol as 'Nanoglue'," Naval Research Laboratory, American Physical Society (Mar. 2000).

Ming-Zhi, et al., "A novel fabrication of meso-porous silica film by sol-gel of TEOS," Journal of Zhejiang University Science 427-442 (2004).

* cited by examiner

COMPOSITE NANOPARTICLES FOR ROOFING GRANULES, ROOFING SHINGLES CONTAINING SUCH GRANULES, AND PROCESS FOR PRODUCING SAME

CROSS-REFERENCE TO RELATED APPLICATION

This application claims the benefit of U.S. Provisional Application No. 61/264,034 filed Nov. 24, 2009.

BACKGROUND OF THE INVENTION

1. Field of the Invention

The present invention relates to asphalt roofing shingles, protective granules for such shingles, and processes for making such granules and shingles.

2. Brief Description of the Prior Art

Pigment-coated mineral rocks are commonly used as color granules in roofing applications to provide aesthetic as well as protective functions to the asphalt shingles. Dark blotches or streaks sometimes appear on the surfaces of asphalt shingles, especially in warmer humid climates, because of the growth of algae and other microorganisms. The predominant species responsible is *Gloeocapsa magma*, a blue-green algae. Eventually, severe discoloration of the entire roof can occur.

Various methods have been used in an attempt to remedy the roofing discoloration. For example, topical treatments with organic algaecides have been used. However, such topical treatments usually have only short term effectiveness, typically one to two years. Another approach is to add algaecidel metal oxides to the color granule coatings. This approach is likely to provide longer protection, for example, as long as ten years.

Companies, including Minnesota Mining and Manufacturing (3M) and GAF Materials Corporation/ISP Mineral Products Inc., have commercialized several algaecide granules that are effective in inhibiting algae growth.

A common method used to prepare algae-resistant (AR) roofing granules generally involves two major steps. In the first step, metal oxides such as cuprous oxide and/or zinc oxide are added to a clay and alkali metal silicate mixture. The mixture in turn is used to coat crushed mineral rocks. The mixture is rendered insoluble on the rock surfaces by firing at high temperatures, such as about 500° C., to provide a ceramic coating. In the second step, the oxide-covered rocks are coated with various color pigments to form colored algae-resistant roofing granules. The algae-resistant granules, alone, or in a mixture with conventional granules, are then used in the manufacture of asphalt shingles using conventional techniques. The presence of the algae-resistant granules confers algae-resistance on the shingles.

Roofing granules typically comprise crushed and screened mineral materials, which are subsequently coated with a binder containing one or more coloring pigments, such as suitable metal oxides. The binder can be a soluble alkaline silicate that is subsequently insolubilized by heat or by chemical reaction, such as by reaction between an acidic material and the alkaline silicate, resulting in an insoluble colored coating on the mineral particles.

U.S. Pat. No. 3,507,676 discloses roofing granules containing zinc, zinc oxide, or zinc sulfide, as an algaecide and fungicide.

Algae resistant shingles are disclosed, for example, in U.S. Pat. No. 5,356,664 assigned to Minnesota Mining and Manufacturing Co., which discloses the use of a blend of algae-resistant granules and non-algae-resistant granules. The algae-resistant granules have an inner ceramic coating comprising cuprous oxide, and an outer seal coating initially devoid of copper.

Algae resistant roofing granules are also disclosed in U.S. Patent Publications 2004-0258835 A1, 2004-0255548 A1, 2007-0148342 A1, 2007-0148340 A1, and 2008-0118640 A1.

Nanoparticles are known to have interesting properties due to their small particle size and their large surface area and, in some cases, high aspect ratios. For instance, nano titanium dioxide and nano zinc oxide are widely used as UV blockers or for self-cleaning surfaces due to their photocatalytic effect; and nano-silver particles have been used as biocides in textiles, medical devices, etc. However, to incorporate the nanoparticles in an inorganic coating matrix has been a challenge, particularly when considering dispersing and handling such particles of nano-size. In addition, nanoparticles can easily become airborne and easily absorbed by the operator handling the nanoparticles, thus posing potentially serious but currently unknown health or safety issues.

Nanoparticles that are pre-dispersed in liquid medium are commercially available. However, they may not be suitable for some coating applications due to the presence of organic dispersants. Also, such pre-dispersed nanoparticles may require additional processing at a higher cost for use in some coatings applications. One approach to associate nanoparticles into micro-size particles is described in European patent application EP 1889810 A1 and in U.S. Patent Publication 2009/0131517 A1, which disclose dispersing nanoparticles of silver and/or copper and/or their oxides in silica using a flame spray pyrolysis technique to provide antibacterial and antifungal materials.

There is a continuing need for algae-resistant roofing products having algaecide leaching rates that can be controlled so that the roofing products can be tailored for specific local conditions.

SUMMARY OF THE INVENTION

The present invention provides composite nanoparticles which can be used to provide roofing granules, sheet-roofing products such as asphalt shingles. The present invention also provides processes for making composite nanoparticles, and for making roofing granules and sheet-roofing products.

Advantageously, the present invention provides a method to associate nanoparticles into micro or macro sizes so that the nanoparticles can be handled easily and easily incorporated into inorganic coating systems while dispersing them at the same time, and maintaining them in a dispersed state.

Thus, the present invention provides a process for preparing roofing granules, the process comprising: providing granule cores; providing a coating material; coating the granule cores with the coating material to form a coating layer having an exterior surface; including composite nanoparticles in the coating layer; and curing the coating layer.

In one aspect, the present invention provides a process for preparing roofing granules wherein the composite nanoparticles are dispersed in the coating material prior to coating the granule cores with the coating material. In another aspect, the present invention provides a process for preparing roofing granules wherein the composite nanoparticles are applied to the exterior surface of the coating layer.

In one embodiment, the process for preparing roofing granules of the present invention further comprises: providing nanoparticles; providing a carrier material; coating the nanoparticles with the carrier material, the carrier material being dispersible in the coating material; and aggregating the coated nanoparticles to form green composite nanoparticles. In this embodiment, the process preferably further comprises sizing the green composite nanoparticles to form green composite nanoparticles having a predetermined average size.

In another embodiment, the process for preparing roofing granules of the present invention further comprises providing nanoparticles; providing carrier material; dispersing the nanoparticles in the carrier material, the carrier material being dispersible in the coating material; and forming carrier particles from the carrier material including the dispersed nanoparticles, the carrier particles including the composite nanoparticles.

In another embodiment, the process for preparing roofing granules of the present invention further comprises providing nanoparticles; providing carrier material; dispersing the nanoparticles in the carrier material, the carrier material being dissolvable in the coating material; and forming carrier particles from the carrier material including the dispersed nanoparticles, and the carrier particles including the composite nanoparticles. In this embodiment, the carrier material dissolves away from the nanoparticles leaving the nanoparticles distributed in the coating material and the carrier becomes a part of the coating material.

In yet another embodiment, the process for preparing roofing granules of the present invention further comprises providing nanoparticles; providing carrier particles having an exterior surface, the carrier particles including carrier material dispersible in the coating material; and adhering the nanoparticles to the exterior surface of the carrier particles.

In still another embodiment, the process for preparing roofing granules of the present invention further comprises providing nanoparticles; providing carrier particles; mixing the nanoparticles and the carrier particles, the carrier particles including carrier material dispersible in the coating material; and aggregating the carrier particles, the nanoparticles being entrapped among the aggregated carrier particles.

In another embodiment, the process for preparing roofing granules of the present invention further comprises providing nanoparticles; providing porous carrier particles, the carrier particles including carrier material dispersible in the coating material; and entrapping the nanoparticles in the pores of the carrier particles.

Preferably, the process for preparing roofing granules according to the present invention further comprises forming composite nanoparticles including nanoparticles, the nanoparticles being selected from the group comprising silver, silver oxide, copper, copper oxide, zinc, zinc oxide, and titania nanoparticles.

In one aspect, the process for preparing roofing granules according to the present invention further comprises forming composite nanoparticles including at least one carrier material, the at least one carrier material comprising at least one metal silicate. Preferably, when the coating material employed comprises an alkali metal silicate, the at least one metal silicate is preferably sodium silicate. In another aspect, the process for preparing roofing granules according to the present invention further comprises forming composite nanoparticles including at least one carrier material, the at least one carrier material comprising silica.

Preferably, the carrier material is selected to provide shielding of the nanoparticles from the high alkaline or reactive or abrasive environments of the coating materials.

Thus, in one aspect the present invention provides roofing granules comprising copper-based nanoparticles.

In another aspect, the process for preparing roofing granules according to the present invention further comprises forming composite nanoparticles including at least one curing agent for a predetermined coating binder. Preferably, when the coating material comprises alkali metal silicate, the curing agent is selected from the group consisting of kaolin clays, metal phosphates, aluminum fluoride, sodium fluorosilicates, zinc oxides and, metal oxides with leachable multivalent ions in alkaline environment.

In yet another aspect, the process for preparing roofing granules according to the present invention further comprises forming composite nanoparticles including at least one functional material. Preferably, the at least one functional material is selected from the group consisting of colorant pigments, solar reflective pigments, near infrared reflective pigments, photocatalytic particles, organic biocides, inorganic biocides, and algaecides.

Accordingly, in one aspect the present invention provides roofing granules comprising a granule core having an exterior surface; a coating layer covering the exterior surface of the granule core, and; nanoparticles dispersed in the coating material.

In another aspect, the present invention provides roofing granules comprising: a granule core; a coating layer covering the granule core and having an exterior surface, and; nanoparticles dispersed on the exterior surface of the coating layer.

In another aspect, the present invention provides processes for preparing composite nanoparticles. In one embodiment of this aspect, the present invention provides a process for preparing composite nanoparticles comprising: providing nanoparticles; providing porous carrier particles; and entrapping the nanoparticles in the pores of the carrier particles.

In another aspect, the present invention provides a process for preparing composite nanoparticles comprising: providing nanoparticles; providing carrier particles having an exterior surface; and adhering the nanoparticles to the exterior surface of the carrier particles.

In another aspect, the present invention provides a process for preparing composite nanoparticles comprising: providing nanoparticles; providing carrier particles; and aggregating the carrier particles to form carrier particle clusters, the nanoparticles being trapped within the carrier particle clusters.

In another aspect, the present invention provides composite nanoparticles including carrier particles having an exterior surface wherein the nanoparticles are adhered to the exterior surface of the carrier particles; the carrier particles are aggregated to form carrier particle clusters, the nanoparticles being trapped within the carrier particle clusters. Alternatively, the carrier material particles are porous, the nanoparticles being trapped within the pores of the carrier material particles. In such composite nanoparticles, it is preferred that the nanoparticles be selected from the group consisting of silver, silver oxide, copper, copper oxide, zinc, zinc oxide, and titania nanoparticles. In one aspect, the carrier material preferably comprises at least one metal silicate, preferably sodium silicate. In another aspect, the composite nanoparticles further comprise at least one curing agent for a predetermined coating binder, preferably selected from the group consisting of kaolin clays, metal phosphates, aluminum fluoride, sodium fluorosilicates, zinc oxides, and metal oxides with leachable multivalent ions in alkaline environment. In another aspect, the composite nanoparticles preferably further comprise at least one functional material. Preferably, the at least one functional material is selected from the group consisting of colorant pigments, solar reflective pigments, near infrared reflective pigments, photocatalytic particles, organic biocides, inorganic biocides, and algaecides.

Preferably the composite nanoparticles of the present invention have an average size of from about 0.1 micrometers to about 100 micrometers, and more preferably an average size of from about 0.5 micrometers to about 0.5 millimeters.

Preferably, the composite nanoparticles of the present invention have an average number density of nanoparticles in the composite nanoparticles is from about $1\times10^{13}$ nanoparticles per gram of carrier material to about $5\times10^{14}$ nanoparticles per gram of carrier material.

Preferably, the composite nanoparticles of the present invention have an average weight density of nanoparticles in the composite nanoparticles of from about 0.05 grams of nanoparticles per gram of carrier material to about 0.7 grams of nanoparticles per gram of carrier material.

The present invention also provides bituminous sheet-roofing material comprising roofing granules of the present invention, and processes for making such roofing material.

DETAILED DESCRIPTION

The present invention provides for the introduction of desirable nanoparticles into an inorganic coating by either encapsulating the nanoparticles in a dissolvable carrier to form larger particles, such as microparticles, or by associating the nanoparticles in dispersible, preferably dissolvable, carrier particles to form micro-size aggregates. Thus, although the nanoparticles will be carried along by the dispersible carriers in a "micro" or "macro" dry phase, avoiding the need for the handling of free nanoparticles, they will be dispersed into the coating when carrier material is dissolved or dispersed in the coating material.

As used in the present specification and claims, "microparticles" are particles having an average dimension from 0.1 micrometers (100 nanometers) to 100 micrometers, and "nanoparticles" are particles having an average dimension from 0.1 nanometers to 100 nanometers.

Nanoparticles for use in the present invention can be prepared by any of a number of methods. In some cases, preparative methods result in nanoparticle aggregates, in which nanoparticles are dispersed in a carrier material. Methods for preparing composite nanoparticles for use in preparing roofing granules according to the present invention include both methods for preparing composite nanoparticles known in the prior art and methods according to the present invention for preparing composite nanoparticles.

Nanoparticle aggregates in micron sizes containing nano silver particles can be made using a spray flame pyrolysis process, as in the case of HeiQ AGS-20 powder (commercially available from HeiQ Materials AG, Zurich, Switzerland). The carrier particles in this case are amorphous silica particles. The nano silver particles incorporated in the micro composite particles are easily and safely handled.

Other examples of nanoparticles that can be used in making composite nanoparticles including copper, copper oxide, zinc, and/or zinc oxide, are described in European Patent Application EP 1889810 A1 and European Patent in EP 1846327 B1. In this case, the composite particles, including domains of nano copper, or nano copper oxide, or nano zinc, or nano zinc oxide, are dispersed in an inorganic granule coating.

U.S. Pat. No. 7,031,590 describes a technique for preparing nanoparticles comprising metallic ion active elements in a predetermined matrix by chemical synthesis. A sol-gel process is used followed by laser ablation to control the particle size, for subsequent use in preparing improved optical guides in which the nanoparticles are incorporated into an optical fiber core. The metallic active elements are preferably chosen from the rare earths and the transition elements. The predetermined matrix can be silica or an aluminosilicate. Thus, this technique can be used to prepare composite nanoparticles of silver, zinc or other transition element nanoparticles dispersed in a silica or aluminosilicate matrix.

Nanoparticles can be prepared using aerosol techniques. Precursor materials can be dispersed either in vapor or in liquid droplets to form aerosols. Nanoparticles can be synthesized in such aerosols under ambient conditions (such as by the aero-sol-gel process), by heating an aerosol stream in a tubular oven, or by pyrolysis of the aerosol in a flame.

For example, titanium dioxide nanoparticles can be prepared using the spray flame process disclosed in U.S. Pat. No. 7,217,407, incorporated herein by reference. Similarly, antibacterial silicon dioxide particles doped with silver are disclosed in U.S. Pat. No. 6,872,402, incorporated herein by reference.

In another example, an organotitanium compound or titanium chloride is included in the feed for flame spray pyrolysis to produce titania nanoparticles in association with a silica composite body. A process similar to that of the above-mentioned European patent and application can be employed, but taking into account the compositional control used in making optical fiber preforms, such as described in U.S. Pat. No. 7,657,142 incorporated herein by reference, or U.S. Pat. No. 7,031,590 incorporated herein by reference, wherein optical fibers including nanoparticle domains are disclosed. Techniques such as outer vapor deposition (OVD) or vapor axial deposition (VAD), such as used in preparation of porous optical fiber soot preforms prior to sintering, dehydration and consolidation, can be used to prepare composite nanoparticles, with modification to collect the soot of composite nanoparticle composite particles rather than building up a large porous mass which is later consolidated to continuous glass element. The flame-spraying method to produce multicomponent particles, which is described in International Application WO 0020346 A1, incorporated hereby reference, can be modified to collect the composite particles as a powder rather than have them collect on a target substrate as in outside vapor deposition. Thus, composite nanoparticles ("composite particles") including titania nanoparticles dispersed in a silica matrix can be used as carrier particles to disperse the titania nanoparticles in a granule coating. In this case, the composite nanoparticles can be mixed with an alkali metal silicate coating binder, and the mixture can be subsequently applied to suitable granule cores, and heated to cure the coating binder. Heating the coating composition including the dispersed composite nanoparticles will ultimately dissolve the silica carrier particles and leave the titania nanoparticles dispersed in the coating layer.

Nanoparticles can also be prepared using solution techniques. For example, U.S. Pat. No. 6,548,264, incorporated herein by reference, discloses a process for preparing nanoparticles coated with silica. The process employs a microemulsion to produce nanoparticle cores of a predetermined, uniform size and shape. The cores are subsequently coated with silica using a silicizing agent, a reactive silicate such as tetraethylorthosilicate or aminopropyltrimethoxysilane. The nanoparticle cores can be made of a metal such as silver, or a metal salt. Subsequently, the exterior silica surface of the nanoparticles can be functionalized. For example, a silanization agent such as trimethylsilypropyldiethlentriamine can be used to provide primary amine groups on the silica surface. Subsequently, the primary amine groups can be reacted to provide the desired functionality.

Silica-coated nanoparticles can be aggregated subsequently for use in the present invention, or used to prepare roofing granules without prior aggregation. In the alternative, nanoparticles can be aggregated before silica coating, to provide composite nanoparticles for use in the present invention.

The carrier material used to form the composite nanoparticles is preferably dissolvable in or dispersible in, and compatible with, the coating binder used in preparing the roofing granules of the present invention. Thus, the nanoparticle aggregates can be dispersed in the coating binder used to form a coating layer on the mineral particles, or cores used to form roofing granules according to the present invention. Preferably, the carrier material will not produce any negative effects or adversely affect the performance of the coating binder. Preferably, the carrier will enhance the coating binder system and become an integral part of the coating layer.

Conventionally, roofing granules are prepared using a metal silicate coating binder. The roofing granules of the present invention can be prepared through traditional granule preparation methods, such as those disclosed in U.S. Pat. No. 2,981,636, incorporated herein by reference. Thus, in preparing roofing granules according to the present invention, an exterior coating layer is applied to the base particles. The exterior coating layer includes a suitable coating binder. The coating binder can be an inorganic or organic material, and is preferably formed from a polymeric organic material or a silicaceous material, such as a metal-silicate binder, for example an alkali metal silicate, such as sodium silicate. When a metal-silicate binder is employed in the preparation of roofing granules of the present invention, the binder preferably includes a heat-reactive aluminosilicate material, such as clay, preferably, kaolin. Alternatively, the metal silicate binder can be insolubilized chemically by reaction with an acidic material, for example, ammonium chloride, aluminum chloride, hydrochloric acid, calcium chloride, aluminum sulfate, and magnesium chloride, such as disclosed in U.S. Pat. Nos. 2,591,149, 2,614,051, 2,898,232 and 2,981,636, each incorporated herein by reference, or other acidic material such as aluminum fluoride. In another alternative, the binder can be a controlled release sparingly water soluble glass such as a phosphorous pentoxide glass modified with calcium fluoride, such as disclosed in U.S. Pat. No. 6,143,318, incorporated herein by reference.

Thus, when the coating binder employed is a metal silicate binder, the carrier material for the composite nanoparticles is preferably dissolvable or dispersible in the metal silicate. In this case, the carrier material is preferably a metal silicate, such as an alkali metal silicate, and preferably sodium silicate. Thus, to form a roofing granule having nano silver as a biocide suitable for roofing applications, one can add HeiQ AGS-20 powder to the alkali metal silicate binder to form the coating layer containing nano silver. In this case, a metal silicate binder with an increased alkali to silica ratio should be used. As the micro composite particles containing silica carrier and nano silver are added to the metal silicate binder, the silica carrier will be dissolved and thus disperse the nano silver into the coating. The composite particles act as a carrier to deliver nanoparticles into the matrix of the coating. The silica support in the composite particles dissolves into the coating composition, leaving nanoparticles distributed throughout the coating. Further, the silica ratio will increase to help stabilize the coating for better durability and film-forming properties. The coating can then be used to coat the roofing granules according to current art in producing roofing granules for shingle applications. The coated granules can then be further cured in elevated temperatures to render them suitable for long-term durability.

In one aspect, the carrier material can include a curing agent for the coating binder, and will cure the coating binder while dissolving to disperse the nanoparticles.

In another aspect, the carrier material can contain other functional additives or fillers, such as colorant pigments, solar reflective pigments, near infrared reflective particles, photocatalytic particles, organic or inorganic biocides, or algaecides. In this aspect, the carrier material can aid in dispersing such additives in the coating layer.

The base particles employed in the process of preparing the granules of the present invention are preferably chemically inert materials, such as inert mineral particles. The mineral particles, which can be produced by a series of quarrying, crushing, and screening operations, are generally intermediate between sand and gravel in size (that is, between about 8 US mesh and 70 US mesh), and preferably have an average particle size of from about 0.2 mm to about 3 mm, and more preferably from about 0.4 mm to about 2.4 mm.

In particular, suitably sized particles of naturally occurring materials such as talc, slag, granite, silica sand, greenstone, andesite, porphyry, marble, syenite, rhyolite, diabase, greystone, quartz, slate, trap rock, basalt, and marine shells can be used, as well as recycled manufactured materials such as crushed bricks, concrete, porcelain, fire clay, proppants, and the like.

Solid and hollow glass spheres are available, for example, from Potters Industries Inc., P.O. Box 840, Valley Forge, Pa. 19482-0840, such as SPHERIGLASS® solid "A" glass spheres product grade 1922 having a mean size of 0.203 mm, product code 602578 having a mean size of 0.59 mm, BALLOTTINI impact beads product grade A with a size range of 600 to 850 micrometers (U.S. Sieve size 20-30), and QCEL hollow spheres, product code 300 with a mean particle size of 0.090 mm. Glass spheres can be coated with a suitable coupling agent if desired for better adhesion to the binder of the coating composition.

Suitable inert base particles, for example, mineral particles with size passing #8 mesh and retaining on #70 mesh, can be coated with a combination of a metal-silicate binder, kaolin clay, composite nanoparticles, color pigments such as metal oxide pigments to reach desirable colors, and biocidal particles, followed by a heat treatment to obtain a durable coating.

When the coated granules are fired at an elevated temperature, such as at least 800 degrees F., and preferably at 1,000 to 1,200 degrees F., the clay binder densifies to form strong particles. Preferably, the temperature employed is low enough to avoid oxidation of silver and or silver compounds employed in the biocidal particles.

In some embodiments of the present process, the coated granules are fired in an inert atmosphere in order to minimize and/or control oxidation.

Examples of clays that can be employed in the process of the present invention include kaolin, other aluminosilicate clays, Dover clay, bentonite clay, etc.

In the alternative, a suitable siliceous binder can be formed from sodium silicate, modified by the addition of sodium fluorosilicate, aluminum fluoride, and Portland cement.

The roofing granules of the present invention can be colored using conventional coatings pigments. Examples of coatings pigments that can be used include those provided by the Color Division of Ferro Corporation, 4150 East 56th St., Cleveland, Ohio 44101, and produced using high temperature calcinations, including PC-9415 Yellow, PC-9416 Yellow, PC-9158 Autumn Gold, PC-9189 Bright Golden Yellow, V-9186 Iron-Free Chestnut Brown, V-780 Black, V0797 IR Black, V-9248 Blue, PC-9250 Bright Blue, PC-5686 Turquoise, V-13810 Red, V-12600 Camouflage Green, V-12560 IR Green, V-778 IR Black, and V-799 Black.

The proportion of nanoparticles in the target nanoparticle-containing roofing granules can be adjusted depending on a number of factors, such as the intended use of the roofing products manufactured using the target nanoparticle-containing roofing granules, the expected environmental conditions at the site where the roofing products including the target nanoparticle-containing roofing granules are to be installed, the proportion of nanoparticles and thickness(es) of the coating layer(s) of the target roofing granules, the proportion of nanoparticle-containing roofing granules to conventional roofing granules employed in the roofing product, etc.

Referring now to the drawings, in which like reference numerals refer to like elements in each of the several views, there are shown schematically in FIGS. 1, 2, 3, 4 and 5 examples of composite nanoparticles which can be employed in preparing roofing granules according to the process of the present invention.

Figure 1:
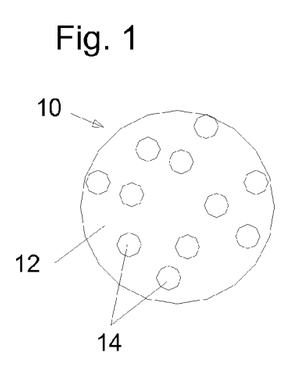
FIG. 1 is a schematic representation of a type of prior art composite nanoparticle employed in the present invention.

FIG. 1 is a schematic representation of a type of prior art composite nanoparticle 10 employed in the present invention. The composite nanoparticle or composite particle 10 includes a plurality of silver nanoparticles 14, such as about 20 weight percent, dispersed in an amorphous silica matrix 12. Nanoparticle aggregates 10 are available from HeiQ Materials AG as AGS-20 high performance antimicrobial silver additive, and can be prepared, for example, by the process disclosed in European Patent 1,846,327 B1 and European Patent Application 1,889,810 A1.

Figure 2:
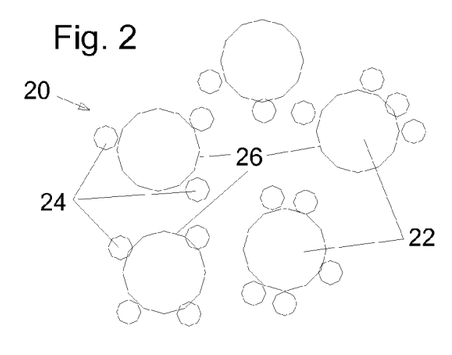
FIG. 2 is a schematic representation of a first type of a composite nanoparticle of the present invention.

FIG. 2 is a schematic representation of another type of composite nanoparticle 20 employed in the present invention. The composite nanoparticle or composite particle 20 includes a plurality of silver nanoparticles 24, such as about 20 weight percent, adhered to the exterior surface 26 of amorphous silica particles 22. The nanoparticles 24 can be adhered to the exterior surface 26 by physical forces, or chemically linked to the exterior surface 26 by suitable linking agents (not shown).

Figure 3:
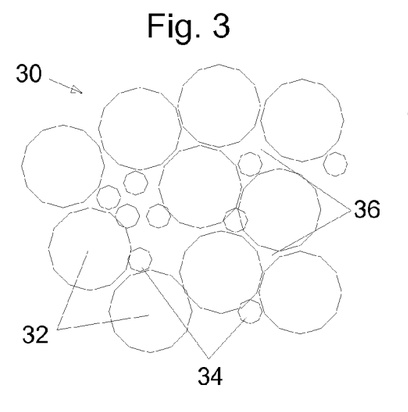
FIG. 3 is a schematic representation of a second type of a composite nanoparticle of the present invention.

FIG. 3 is a schematic representation of yet another type of composite nanoparticle 30 employed in the present invention. The composite nanoparticle or composite particle 30 includes a plurality of silver nanoparticles 34, physically entrapped in the interstices 36 formed among a group of amorphous silica particles 32.

Figure 4:
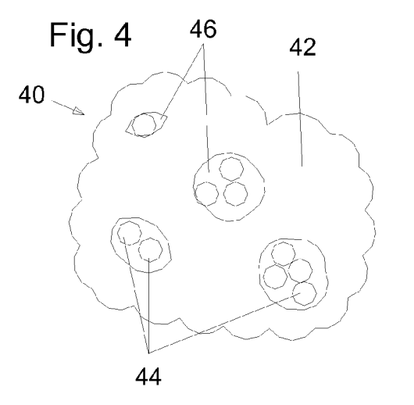
FIG. 4 is a schematic representation of a third type of a composite nanoparticle of the present invention.

FIG. 4 is a schematic representation of still another type of composite nanoparticle 40 employed in the present invention. The composite nanoparticle or composite particle 40 includes a plurality of silver nanoparticles 44, physically entrapped in the pores 46 formed in the particles 42.

Figure 5:
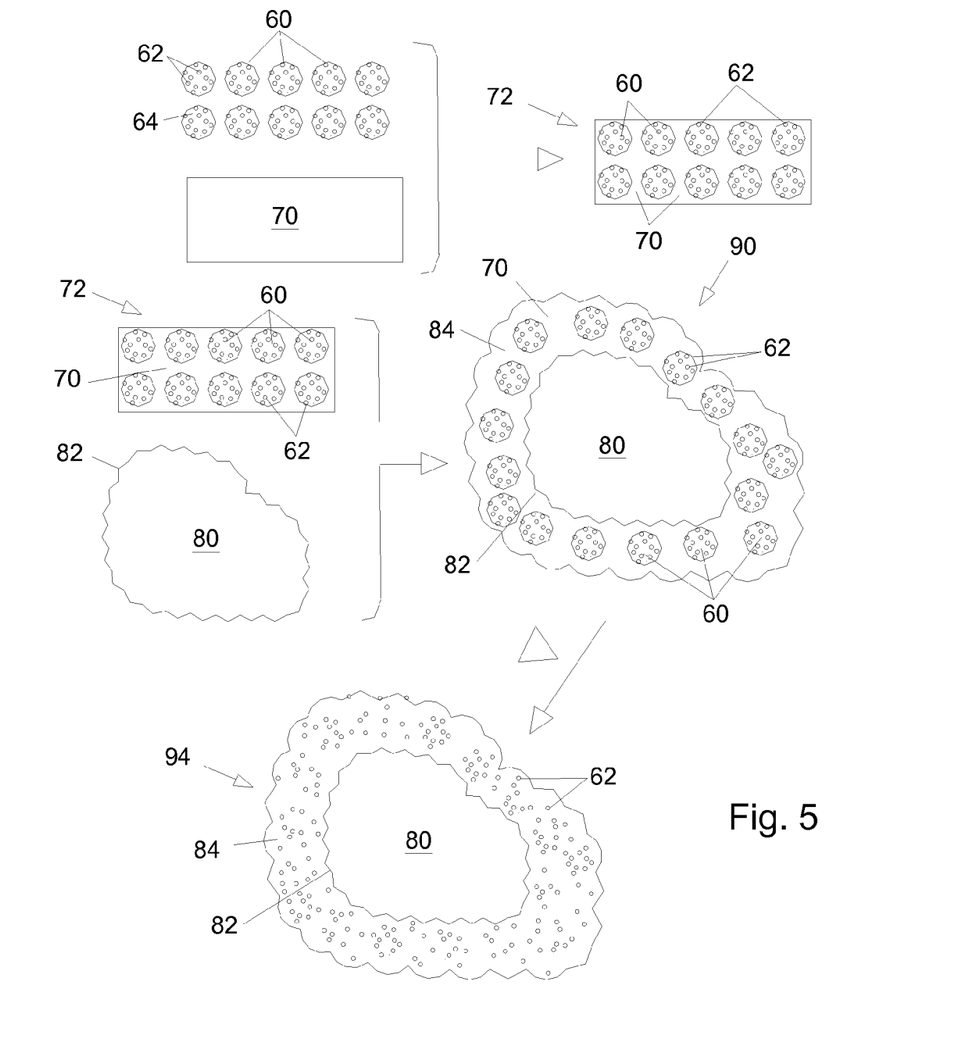
FIG. 5 is a schematic illustration of a process for preparing roofing granules according to the present invention

FIG. 5 is a schematic illustration of a process for preparing roofing granules 94 according to the present invention. Nanoparticle aggregates 60, including silver nanoparticles 62 dispersed in an amorphous silica matrix 64, are mixed with a coating binder 70 including sodium silicate, clay, and a metal oxide colorant to give a coating composition 72 in which the composite nanoparticle aggregates 60 are dispersed. The coating composition 72 is applied to the exterior surface 82 of mineral core particles 80 to form a layer 84 on the mineral core particles 80 to provide green roofing granules 90. The green roofing granules 90 are subsequently fired to fuse the sodium silicate, clay and the silica and thus to dissolve the silica matrix of the nanoparticle aggregates 60 in the coating binder 70 and thus disperse the silver nanoparticles 62 and provide cured roofing granules 94. It will be understood that in some embodiments the pH of the coating binder 70 may be such that the silica matrix 64 dissolves into the binder 70 dispersing the nanoparticles 62 prior to the firing of the green granules 90.

The roofing granules of the present invention can be employed in the manufacture of roofing products, such as asphalt shingles and bituminous membranes, using conventional roofing production processes. Typically, bituminous roofing products are sheet goods that include a non-woven base or scrim formed of a fibrous material, such as a glass fiber scrim. The base is coated with one or more layers of a bituminous material such as asphalt to provide water and weather resistance to the roofing product. One side of the roofing product is typically coated with mineral granules to provide durability, reflect heat and solar radiation, and to protect the bituminous binder from environmental degradation. The antimicrobial roofing granules of the present invention can be mixed with conventional roofing granules, and the granule mixture can be embedded in the surface of such bituminous roofing products using conventional methods. Alternatively, the antimicrobial roofing granules of the present invention can be substituted for conventional roofing granules in the manufacture of bituminous roofing products.

Bituminous roofing products are typically manufactured in continuous processes in which a continuous substrate sheet of a fibrous material such as a continuous felt sheet or glass fiber mat is immersed in a bath of hot, fluid bituminous coating material so that the bituminous material saturates the substrate sheet and coats at least one side of the substrate. Roofing granules are then distributed over selected portions of the top of the sheet, and the bituminous material serves as an adhesive to bind the roofing granules to the sheet when the bituminous material has cooled. The reverse side of the substrate sheet can then be coated with an anti-stick material such as a suitable mineral powder or a fine sand. The sheet can then be cut into conventional shingle sizes and shapes (such as one foot by three feet rectangles), slots can be cut in the shingles to provide a plurality of "tabs" for ease of installation and aesthetic effect, additional bituminous adhesive can be applied in strategic locations and covered with release paper to provide for securing successive courses of shingles during roof installation, and the finished shingles can be packaged. More complex methods of shingle construction can also be employed, such as building up multiple layers of sheet in selected portions of the shingle to provide an enhanced visual appearance, or to simulate other types of roofing products. Alternatively, the sheet can be formed into membranes or roll goods for commercial or industrial roofing applications.

The bituminous material used in manufacturing roofing products according to the present invention is derived from a petroleum-processing by-product such as pitch, "straight-run" bitumen, or "blown" bitumen. The bituminous material can be modified with extender materials such as oils, petroleum extracts, and/or petroleum residues. The bituminous material can include various modifying ingredients such as polymeric materials, such as SBS (styrene-butadiene-styrene) block copolymers, resins, flame-retardant materials, oils, stabilizing materials, anti-static compounds, and the like. Preferably, the total amount by weight of such modifying ingredients is not more than about 15 percent of the total weight of the bituminous material. The bituminous material can also include amorphous polyolefins, up to about 25 percent by weight. Examples of suitable amorphous polyolefins include atactic polypropylene, ethylene-propylene rubber, etc. Preferably, the amorphous polyolefins employed have a softening point of from about 130 degrees C. to about 160 degrees C. The bituminous composition can also include a suitable filler, such as calcium carbonate, talc, carbon black, stone dust, or fly ash, preferably in an amount from about 10 percent to 70 percent by weight of the bituminous composite material.

The following examples are provided to better disclose and teach processes and compositions of the present invention. They are for illustrative purposes only, and it must be acknowledged that minor variations and changes can be made without materially affecting the spirit and scope of the invention as recited in the claims that follow.

EXAMPLE 1

Roofing granules can be prepared by using 1 kg of US #11 grade mineral particles as a base followed by coating with a mixture of 35 g sodium silicate binder from Occidental Petroleum Corp., 17.5 g of kaolin clay from Unimin Corp., 0.768 g of HeiQ AGS-20 powder (HeiQ Materials AG, Zurzach, Switzerland). This is to provide an active silver level of 0.5% for achieving effective algaecidel dosage. The coated granules are heat-treated in a rotary drum at temperatures between 480° C.-510° C. in order to cure the coating and to disperse the silver nanoparticles.

EXAMPLE 2

Nanosilver particles were incorporated into a silica matrix and then dispersed into a roofing granule coating by the following procedures. 5 mL of nano-silver particles in aqueous suspension (157 nm mean particle diameter, #675318 from Sigma-Aldrich at 0.25 mM conc.) was slowly added to 1.23 gm of fumed silica (S5505-100G from Sigma-Aldrich) and mixed with a spatula in a beaker. The adding of nanosilver aqueous suspension improved the handleability of the fumed silica from its fluffiness into a cohesive small pellet or balls that can be transported easily without the issue of airborne nanoparticles or fluffy mass. The resulting mixture had a slight transparent and moist mass look.

Roofing granules containing nano-silver particle were then prepared by coating suitable mineral particles (#11 grading roofing granule, available from CertainTeed Corp., Norwood, Mass.) with the mixture above in the following steps. A coating was prepared by mixing 17.55 gm of sodium silicate (Grade 40 from Oxychem, Dallas, Tex.), 8.10 gm of water, 8.75 gm of kaolin clay (Royale air-flow clay from Unimin Corp., Hephzibah, GA), and 1.42 gm of the nano-silver/silica mixture in a propeller mixer at 300~400 rpm until a uniform coating was obtained. Some shear from the mixer may be needed to break and dissolve the mixture. Once dissolved, the coating had a uniform appearance and no gel formation was noticed. This is good indication that the dispersed nano-silver particles did not react with the binder, which would not be the case if they were directly introduced into the coating without the silica matrix. The coating was then poured into a plastic bottle containing 500 gm of the mineral particles and then blended together by tumbling the bottle for five minutes. The granules were found to be well coated and no agglomeration was observed. The resultant granules were then dried in the air and were heat treated at elevated temperatures to 500 C. to cure the binder.

The resultant granules had a color reading of $L^*=49.21$, $a^*=1.08$, $b^*=5.09$ as measured by HunterLab Labscan EX colorimeter (D65 illumination and 10° observer); and an alkalinity number of 0.61 according to the granule test method #7 of ARMA Granule Test Procedures. Also, the coating had a better scratch resistance due to the addition of silica, as evidenced by needle scratching observation under an optical microscope, when compared to typical roofing granules with similar coating without the additional silica.

EXAMPLE 3

Nano zinc oxide particles, which are known to have algaecide function in roofing granules, were incorporated into a silica matrix and then dispersed into a roofing granule coating by the following procedures. 15 gm of nano zinc oxide particles (Zeno 30 from Umicore Zinc Chemicals, Belgium) was dispersed in 100 mL of 2-propanol (AA51-4 from Fisher Scientific) by mixing them in a glass bottle. The resultant suspension had a milky white appearance. Good dispersion could be easily achieved by shaking them vigorously. This suspension was then slowly added to 6 gm of fumed silica (S5505-100G from Sigma-Aldrich) and mixed with a spatula in a beaker. The resultant mixture had a bright white appearance and a consistency similar to cream cheese. The mixture was then allowed to dry in a ventilated hood for 24 hours. The resultant mixture had a form of small white pellets or free flowing particles that could be handled easily without stirring up airborne dust.

Roofing granules containing nano zinc oxide particles for algaecide effect were then prepared by coating suitable mineral particles (#11 grading roofing granule, available from CertainTeed Corp., Norwood, Mass.) with the mixture above in the following steps. The coating was prepared by mixing 35 gm of sodium silicate (Grade 40 from Oxychem, Dallas, Tex.), 39.27 gm of water, and 20.72 gm of the above-mentioned mixture in a propeller mixer at 400~500 rpm until a uniform coating was achieved. Due to the large amount of the mixture with silica/nano zinc oxide, additional shear from the mixer was needed to break and dissolve the mixture. Once dissolved, the coating had a uniform appearance without any gel formation. The resulting coating had a milky white color and a consistency similar to tomato sauce with a thixotropic nature. The coating was then poured into a plastic bottle containing 500 gm of the mineral particles and then blended together by tumbling the bottle for five minutes. The granules were found to be coated well. No agglomeration was observed. The resultant granules were then dried in the air and heat-treated at elevated temperatures to 500° C. to cure the binder. The resultant granules contained 3% zinc oxide by weight, which is considered as an effective algaecide in asphalt shingle applications.

The resultant granules had a desirable appearance with a color reading of L*=48.90, a*=3.31, b*=7.84 as measured by HunterLab Labscan EX colorimeter (D65 illumination and 10° observer); and an alkalinity number of 1.27 according to the granule test method #7 of ARMA Granule Test Procedures.

EXAMPLE 4

Nano-silver particles were incorporated into a silica matrix by the following procedures. One gm of nano-silver powder (#576832-5G from Sigma Aldrich) was first dispersed in five mL of deionized water by mixing them in a glass bottle. The resultant suspension had a uniform, brownish appearance with no settling of the nano-silver particles. The suspension was then slowly added to 1.01 gm of fumed silica (S5505-100G from Sigma-Aldrich) and mixed with a spatula in a beaker. This resulted in the cohesion of the fumed silica to form a paste-like mass that was easy to handle and transport. The resultant mixture was air-dried indoors at ambient temperature, and the resulting mixture turned into a brown solid pellet or chunk without airborne dust. This process provided 50 wt % concentration of nano-silver in a silica matrix.

The resultant mixture could then be incorporated into the coating for a roofing granule following the steps in the previous example to achieve a high loading of nano-silver in the coating for algaecidel effects.

Various modifications can be made in the details of the various embodiments of the processes, compositions and articles of the present invention, all within the scope and spirit of the invention and defined by the appended claims.

The invention claimed is:

1. A process for preparing roofing granules, the process comprising:
   (a) providing granule cores;
   (b) providing a coating material;
   (c) coating the granule cores with the coating material to form a coating layer having an exterior surface;
   (d) including composite nanoparticles in the coating layer; and
   (e) curing the coating layer.

2. A process for preparing roofing granules according to claim 1 wherein the composite nanoparticles are dispersed in the coating material prior to coating the granule cores with the coating material.

3. A process for preparing roofing granules according to claim 1, the process further comprising:
   (a) providing nanoparticles;
   (b) providing a carrier material;
   (c) coating the nanoparticles with the carrier material, the carrier material being dispersible in the coating material; and
   (d) aggregating the coated nanoparticles to form green composite nanoparticles.

4. A process according to claim 3 wherein the process further comprises sizing the green composite nanoparticles to form green composite nanoparticles having a predetermined average size.

5. A process for preparing roofing granules according to claim 1 further comprising forming composite nanoparticles including nanoparticles, the nanoparticles being selected from the group comprising silver, silver oxide, copper, copper oxide, zinc, zinc oxide, and titania nanoparticles.

6. A process for preparing roofing granules according to claim 1 further comprising forming composite nanoparticles including at least one carrier material, the at least one carrier material comprising at least one metal silicate.

7. A process for preparing roofing granules according to claim 6 wherein the at least one metal silicate is sodium silicate.

8. A process for preparing roofing granules according to claim 1 further comprising forming composite nanoparticles including at least one curing agent for a predetermined coating binder.

9. A process for preparing roofing granules according to claim 8 wherein the curing agent is selected from the group consisting of kaolin clays, metal phosphates, aluminum fluoride, sodium fluorosilicates, zinc oxides, metal oxides with leachable multi-valent ions in alkaline environment and combinations thereof.

10. A process for preparing roofing granules according to claim 1 further comprises forming composite nanoparticles comprising at least one functional material.

11. A process for preparing roofing granules according to claim 10 wherein the at least one functional material is selected from the group consisting of colorant pigments, solar reflective pigments, near infrared reflective pigments, photocatalytic particles, organic biocides, inorganic biocides, and algaecides.

12. A process for preparing roofing granules according to claim 1 wherein the composite nanoparticles are applied to the exterior surface of the coating layer.

13. A process for preparing roofing granules according to claim 1, the process further comprising:
   (a) providing nanoparticles;
   (b) providing carrier material;
   (c) dispersing the nanoparticles in the carrier material, the carrier material being dispersible in the coating material; and
   (d) forming carrier particles from the carrier material including the dispersed nanoparticles, the carrier particles comprising the composite nanoparticles.

14. A process for preparing roofing granules according to claim 1, the process further comprising:
   (a) providing nanoparticles;
   (b) providing carrier particles having an exterior surface, the carrier particles including carrier material dispersible in the coating material; and
   (c) adhering the nanoparticles to the exterior surface of the carrier particles.

15. A process for preparing roofing granules according to claim 1, the process further comprising:
   (a) providing nanoparticles;
   (b) providing carrier particles;
   (c) mixing the nanoparticles and the carrier particles, the carrier particles including carrier material dispersible in the coating material; and
   (d) aggregating the carrier particles, the nanoparticles being entrapped among the aggregated carrier particles.

16. A process for preparing roofing granules according to claim 1, the process further comprising:
   (a) providing nanoparticles;
   (b) providing porous carrier particles, the carrier particles including carrier material dispersible in the coating material; and
   (c) entrapping the nanoparticles in the pores of the carrier particles.

17. A process for preparing roofing granules according to claim 1 further comprising forming composite nanoparticles including at least one carrier material, the at least one carrier material comprising silica.

\* \* \* \* \*